United States Patent [19]

Blank et al.

[11] Patent Number: 5,462,728
[45] Date of Patent: Oct. 31, 1995

[54] PHARMACEUTICAL COMPOSITIONS

[76] Inventors: Izhak Blank, 4 Simtat Arnon, Kiryat Ono 55000; Alon Blank, 22a Tamar Street, Haifa 34325, both of Israel

[21] Appl. No.: 222,881

[22] Filed: Apr. 5, 1994

[51] Int. Cl.⁶ .................... A61K 7/16; A61K 9/06
[52] U.S. Cl. .................... 424/49; 424/54; 514/900; 514/901; 514/902; 514/944
[58] Field of Search .................... 514/900, 901, 514/902, 944; 424/49, 54

[56] References Cited

U.S. PATENT DOCUMENTS

| | | | |
|---|---|---|---|
| 4,248,855 | 2/1981 | Blank et al. | 424/49 |
| 4,533,540 | 8/1985 | Blank | 514/785 |
| 4,980,150 | 12/1990 | Keith | 424/49 |
| 5,032,384 | 7/1991 | Yeh et al. | 424/49 |
| 5,100,650 | 3/1992 | Carlin et al. | 424/52 |
| 5,139,768 | 8/1992 | Friedman | 424/49 |
| 5,188,821 | 2/1993 | Gaffar et al. | 424/52 |
| 5,318,780 | 6/1994 | Viegas et al. | 523/122 |

*Primary Examiner*—Ronald W. Griffin
*Attorney, Agent, or Firm*—Edwin D. Schindler

[57] ABSTRACT

Composition for the treatment of gingivitis and other afflictions of the oral cavity, as well as for the reduction of dental plaque. These are in the form of gels, solutions or similar forms which comprise a therapeutically active agent in a polymeric carrier which contains a solvent. The nature of the preparation is such that when these are applied to an aqueous environment of the oral cavity, the polymer and the active agent precipitate and form a coating.

6 Claims, No Drawings

PHARMACEUTICAL COMPOSITIONS

FIELD OF THE INVENTION

Compositions for the prevention and treatment of various diseases and other afflications of the oral cavity, such as gingivitis, periodentities and the like, and also for the reduction of the incidence of dental plaque on teeth. The preparations are provided in a liquid or semi-liquid form, suitable for application by brushing and similar techniques, such as solutions, gels or the like. The compositions comprise a therapeutically active component in adequate concentration, in a matrix of a polymer and solvent of such polymer, and the polymer and solvent are such that when coming into contact with the aqueous environment of the oral cavity the polymer, together with the active component, precipitate and form a film at the application site. The term "polymer" covers copolymers and mixtures of suitable physiologically acceptable polymers. The composition can contain further components, such as thickening or viscosity enhancing agent. There is also provided a method for preventing and treating infections of the oral cavity, based on the local application of compositions defined above.

BACKGROUND OF THE INVENTION

At present no completely satisfactory method for preventing or curing gingivitis exists. A number of substances is effective in reducing the infection and its symptoms such as redness, bleeding, etc. Due to the ease of re-infection treatments give only temporary relief unless continued indefinitely. Present treatments have been summarized in "Periodontal Diseases (Bral. M. et al. Dental Clinics of North America 32:2, 217–241, 1988), indicating that antibiotics may lead to the development of resistant strains.

Enzymes in the form of chewing gum are effective in reducing plaque but irritate the soft tissue and have an unpleasant taste.

Listerine contains thymol, eucaliptol, methylsalicilate, benzoic acid and boric acid and three daily one-minute rinses over a two-week study period showed great reduction in plaque and decreases in the severity of gingivitis. Chlorhexidine is more effective in reducing plaque and gingival index scores and slightly less effective in the resolution of gingivitis (Axelsoon P. et al: Efficiency of mouth rinses in inhibiting dental plaque and gingivitis in man. J. Clin. Periodontal 14 205 1987).

Chlorhexidine adheres to various oral surfaces and exerts a prolonged action. A main problem is how to maintain the medication at the site of application for as long as possible. This is difficult in view of the mobility of oral tissues and the rinsing effect of salival fluid. It has been proposed to use Orabase as carrier, but it is difficult to apply to larger areas and in inaccessible locations of the oral cavity.

It has been suggested to introduce fibers filled with antibiotics into periodental pockets.

The present invention provides effective means for applying a suitable agent to oral mucosa and retain it in place.

It has been estimated that there exist more than 400 diseases affecting the oral cavity, many of them of bacterial origin. Amongst these, periodontal disease is probably the most prevalent and in fact is considered to be one of the most widespread of human adult diseases. Most adults above 40–50 years of age suffer from chronic periodontal disease (R. J. Dubos, Editor, "Bacterial and Mycotic infections of Man". 3rd Ed. p645, J. P. Lippincot Co. Phila. 1958) but in many undeveloped countries gingivitis and destructive periodontal disease are prevalent and severe also in the young (Schluger S. et. al: Periodontal Diseases, p.77, Lea and Farbiger, Philadelphia).

Three stages of this disease have been characterized: a) a subacute or chronic inflammation of the gingival margin (margin gingivitis), b) an acute ulcerative variety (vincents gingivitis), and c) periodontal breakdown (Piorrea) which is characterized by progressive development of pockets opening at the inner gingival margin.

This eventually results in weakening of attachment and is the main cause for loss of teeth in the adult stages of life.

The term gingivitis refers to an inflammatory condition of the gingiva. The term periodontitis refers to the condition when progress of lesions results in destruction of periodontal fibers.

The initial lesions are induced by an aggregate of bacteria known as plaque, which is a complex mixture of lipopoly saccharides, cariogenic microorganisms such as Streptococcus mutans, Actinomyces viscous and Lactobacilli, and periodontal microorganisms such as Antino Antinobacillus, Veillonella, Bacteroides, Eikenella, Capnocytophaga and Syrocheta. The amounts of patogens are enormous: it has been demonstrated that there are $1.7 \times 10^{11}$ organisms per net gram of plaque. In order to prevent gingivitis it is important to decrease the formation of plaque and in order to prevent periodontitis it is necessary to control gingivitis. Frequent brushing and cleaning are recognized to be excellent ways for preventing the accumulation of plaque. However, the average person does not generally devote the time and effort required to achieve thorough cleaning. Moreover, even minute amounts of food material left in the interstices between the teeth will constitute an excellent substrate for the growth of pathogens.

SUMMARY OF THE INVENTION

This invention relates to a novel gel-type, or solution type bioadhesive comprising a copolymer matrix containing a therapeutic agent. The composition and properties of these are such that when applied to mucose tissue a film will instantly be formed, which is water-insoluble but water-swellable. The film adheres to moist tissues, such as the gingiva and will stay in place for many hours, gradually releasing the therapeutic agent.

The polymer of such film has to fulfill several conditions:

a) be completely non-toxic and non-irritating;

b) be soluble in a physiologically acceptable solvent such as ethanol, but insoluble in water;

c) have good adhesion to wet mucose tissue, so as to stay in place for several hours;

d) have enough hydrophilicity to absorb water so that it can be easily removed by normal brushing procedures;

e) have good compatibility and be a good solvent for the therapeutic agent. A preferred embodiment of such a polymer can be prepared from polyvinylacetate as main monomer, and a carboxyl containing monomer such as acrylic acid, methacrylic acid maleic anhydride or itaconic acid as comonomer. Other comonomers such as esters of acrylic or methacrylic acid can also be used.

The preferred carboxyl containing monomer is itaconic acid. The copolymer is linear, and is a good solvent for the therapeutic agent which is incorporated in a small quantity compared with the polymer.

Polyvinylacetate is a good solvent and retains certain organic compounds. The copolymer is soluble in ethanol, but insoluble and only swellable in water. A gel can be prepared from such a polymer by dissolving it in ethanol and its viscosity can be adjusted by an appropriate thickener such as hydroxypropylcellulose (Klucel) or similar materials. The preferred therapeutic ingredient, is chlorhexidine. The preferred solvent is ethanol. When such a gel is applied to the mucosa of the oral cavity such as the gingiva or the inner parts of the lips, the salival fluid will dilute the ethanolic gel and precipitate the polymer as film within a few seconds. Such a film adheres to the mucose and slowly releases the chlorhexidine which penetrates the periodontal pockets and crevices thus reducing or eliminating bacterial growth. As indicated previously (Sela J. et. al Oral Surg. 35: 118/1973), chlorhexidine will be reversibly retained in the oral soft tissues. The system performs, in fact as long-acting mouth rinse. The recommended manner of application is at night so that during the sleeping hours it will perform a bacterial effect. In the morning it will be eliminated by brushing the teeth.

There exist many therapeutical agents which are of use for the treatment of infections in the mouth area. (See Bral. M. Antimicrobial Agents in the Prevention and Treatment of Periodontal Diseases, Dental Clinics of North America, Vol., 32 No. 2, p.227, April 1988). Characteristics of these:

1. Elimination of pathogenic bacteria;
2. nondevelopment of resistant bacteria;
3. safety to the oral tissues at the concentrations and dosages recommended;
4. ability to significantly reduce plaque and gingivitis;
5. no staining of teeth or alteration of taste;
6. no adverse effect on teeth or their substitutes;
7. case of use;
8. affordable cost.

Materials which can be used by themselves or in various combinations are, for example, bis-guanidines such as chlorhexidine, antibiotics, fluorides, sanguinarine, quaternary ammonium compounds, phenolic compounds, thymol, eucalyptol, methyl salicylate, benzoates, borates, certain enzymes, metradinazole and other compounds having bactericidal or bacteriostatic properties.

A preferred agent is chlorhexidine in the form of an organic salt such as digluconate, diacetate, diascorbate, etc., or as the free base. It fulfills most of the conditions mentioned above, has a wide spectrum of effectivity and reduces infection quickly without toxicological or other side-effects. The same system can also be used for the systemic delivery of various drugs via the bucal mucosa tissues.

EXAMPLE 1

In a 3-neck glass flask provided with condenser and mechanical stirrer were put, in this order: cyclohexane 100 ml sorbitan monostereate 1 g., vinyl acetate 35 g. methyl methacrylate 4 g. and itaconic acid 1.2 g. The mixture was heated to reflux in an oil bath and 1 g. of lauroyl Peroxide was added as catalyst. After 10 hours a solid Polymer Precipitate had formed which separated from the cyclohexane. The solvent was poured out and the polymer was dissolved in 80 ml of ethanol. The resulting viscous solution was spread over a teflon sheet and dried in an air over at 60° C. The dried polymer was triturated and washed repeatedly with deionized water. It was then dried again. It had an itaconic acid content of 2.3%.

EXAMPLE 2

The same apparatus and procedure as in Example I were used. The materials and quantities were as follows: cyclohexane 100 ml; itaconic acid 2 g. vinyl acetate 40 g. lauroyl peroxide 0.3 g. The itaconic acid content of the final product obtained was 2.89%.

EXAMPLE 3

In an apparatus as described in Example 1, were put: water 360 ml, and polyvinyl alcohol 0.2 g, itaconic acid 10 g, and vinyl acetate; 230 g. containing 1.6 g. of benzoyl peroxide were added portionwise while refluxing. After 20 hours cooled the emulsion and poured into a beaker containing 1.5 liter of concentrated sodium chloride solution. Allowed to settle, filtered and washed with water, and dried in an air oven. The itaconic acid content of the polymer obtained was 3.15%.

EXAMPLE 4

The same procedure as in Example 1 was used, but the materials employed were cyclohexane 300 ml, Acrylic acid 7 g., vinyl acetate 108 g. and lauroyl peroxide 0.9 g. The resulting copolymer contained 6.73% of acrylic acid.

EXAMPLE 5

Same procedure as in Example 1 but using cyclohexane 200 ml, vinyl acetate 72 g. and lauroyl peroxide 0.6 g.

EXAMPLE 6

In a wide-mouth glass flask, closed by a glass cover and provided with mechanical stirring were put in: 68.7 g. of ethanol. Added under vigorous stirring 30 g. of a copolymer prepared as per Example 3, 1.3 g. of Klucel HF (hydroxypropylcellulose) and a solution of 150 mg of chlorhexidine base in 5 ml of ethanol. The resulting gel was used in clinical tests.

Three patients suffering from gingivitis and gingiva bleeding were instructed to apply every night, before sleep, about 10 mg of the gel, by smearing the upper gingiva with a cotton swab. After 7 to 14 days of this treatment, inflammation, redness, bleeding and all other symptoms of gingivitis had disappeared in all patients.

EXAMPLE 7

A series of placebo gels were prepared as per Example 8, using various polymers. The resulting gels were applied to the upper gingiva and residence time and adhesion were evaluated. Results are summarized in the table below:

| Component: | Polymer | Hydrophilic | Adhesion time* |  |
|---|---|---|---|---|
| 1. | 2.3% | It. acid | good | 4–8 |
| 2. | 2.9% | " | " | " |
| 3. | 3.1% | " | " | " |
| 4. | 5.9% | " | " | 2–4 |
| 5. | 6.7% | Ac. acid | " | 1–2 |
| 6. | — |  | none | poor | 1–4 |

*Residence time (in hours) was evaluated visually. Some of these preparations were also made with addition of 1% Titanium dioxide to improve visibility on the gingiva. Adhesion was tested by trying to pull, with a fine pincette, the film from the gingival substrate.

We claim:

1. A composition for the treatment and for the prevention of gingivitis, periodentitis and other afflictions of the oral cavity, said composition comprising solutions and/or gels of a water insoluble or water swellable copolymer of vinyl acetate and a hydrophilic comonomer selected from the group consisting of itaconic, acrylic, methacrylic, fumaric and maleic acid, a physiologically acceptable solvent, and a therapeutically active agent selected from the group consisting of bisguanidines and physiologically acceptable salts thereof, wherein said hydrophilic comonomers constitute from 0.5 to 8% of the copolymer, and wherein upon contact of said solution or gel with the aqueous environment of the oral cavity, a bioadhesive coating of copolymer containing said active agent is precipitated in situ, which retains its activity for a period of hours.

2. The composition according to claim 1, wherein said bisguanidine is chlorohexidine.

3. The composition according to claim 1, further comprising a thickening agent selected from the group consisting of hydroxypropyl cellulose, an alcohol-soluble thickening agent, fumed silica, calcium stearate and magnesium stearate.

4. The composition according to claim 1, wherein said copolymer contains from 92 weight-% vinyl acetate to 98 weight-% vinyl acetate and from 2 to 8 weight-% of itaconic acid and said composition contains from 56 weight-% to 89.4 weight-% of ethanol as solvent.

5. The composition according to claim 1, which comprises an alcoholic solution or gel comprising 10 to 40 weight-% of a copolymer of vinyl acetate and itaconic acid containing 2 to 8 weight-% itaconic acid in the copolymer, 0.5 to 2.5 weight-% of a thickener and from 0.1 to 1 weight-% of chlorohexidine base or salt and 56% to 89.4 weight-% of ethanol.

6. A method for preventing and treating infections of the oral cavity in need of such treatment and for plaque prevention, said method comprising the step of applying to said oral cavity a composition comprising solutions and/or gels of a water insoluble or water swellable copolymer of vinyl acetate and a hydrophilic comonomer selected from the group consisting of itaconic, acrylic, methacrylic, fumaric and maleic acid, a physiologically acceptable solvent, and a therapeutically active agent selected from the group consisting of bisguanidines and physiologically acceptable salts thereof, wherein said hydrophilic comonomers constitute from 0.5 to 8% of the copolymer, resulting in the in situ formation of an adhering film which remains active for a period of hours.

* * * * *